US009217222B2

(12) United States Patent
Huchel et al.

(10) Patent No.: US 9,217,222 B2
(45) Date of Patent: Dec. 22, 2015

(54) PREVENTION OF BODY ODOUR

(75) Inventors: Ursula Huchel, Cologne (DE); Markus Egert, Villingen-Schwenningen (DE); Andreas Bauer, Kaarst (DE); Andreas Gerigk, Erkelenz (DE); Frank Pessel, Dusseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/414,966

(22) Filed: Mar. 8, 2012

(65) Prior Publication Data

US 2012/0164097 A1 Jun. 28, 2012

Related U.S. Application Data

(63) Continuation of application No. PCT/EP2010/061737, filed on Aug. 12, 2010.

(30) Foreign Application Priority Data

Sep. 11, 2009 (DE) ......................... 10 2009 029 370

(51) Int. Cl.

| | |
|---|---|
| ***A61K 8/49*** | (2006.01) |
| ***C07D 277/24*** | (2006.01) |
| ***A61Q 13/00*** | (2006.01) |
| ***C07C 311/60*** | (2006.01) |
| ***D06M 13/00*** | (2006.01) |
| ***C11D 3/00*** | (2006.01) |
| ***C11D 3/32*** | (2006.01) |
| ***C11D 3/34*** | (2006.01) |
| ***C11D 3/50*** | (2006.01) |
| ***D06M 13/352*** | (2006.01) |
| ***D06M 13/432*** | (2006.01) |

(52) U.S. Cl.

CPC ........... *D06M 13/005* (2013.01); *C11D 3/0068* (2013.01); *C11D 3/323* (2013.01); *C11D 3/349* (2013.01); *C11D 3/3481* (2013.01); *C11D 3/50* (2013.01); *D06M 13/352* (2013.01); *D06M 13/432* (2013.01)

(58) Field of Classification Search

None

See application file for complete search history.

(56) References Cited

U.S. PATENT DOCUMENTS

| | | | | |
|---|---|---|---|---|
| 3,966,968 | A * | 6/1976 | Andree et al. ................ | 514/584 |
| 2001/0039250 | A1 | 11/2001 | Howell et al. | |
| 2008/0076804 | A1 * | 3/2008 | Fabricant ...................... | 514/348 |
| 2008/0194454 | A1 | 8/2008 | Morgan et al. | |

FOREIGN PATENT DOCUMENTS

| | | | |
|---|---|---|---|
| DE | 2303761 | A1 | 8/1974 |
| DE | 102007017655 | A1 | 10/2008 |
| DE | 102008010429 | A1 | 8/2009 |
| WO | WO 2005/081811 | A2 | 9/2005 |
| WO | WO 2006/079934 | A2 | 8/2006 |
| WO | WO 2008/101810 | A1 | 8/2008 |
| WO | WO 2008/141765 | A1 | 11/2008 |

OTHER PUBLICATIONS

PCT International Search Report (PCT/EP2010/061737) dated May 11, 2010.

Ejim et al, "Inhibitors of Bacterial Cystathionine Beta-Lyase: Leads for New Antimicrobial Agents and Probes of Enzyme . . . ", J. Med. Chem., 2007, vol. 50, pp. 755-764.

* cited by examiner

*Primary Examiner* — Mina Haghighatian
*Assistant Examiner* — Luke Karpinski
(74) *Attorney, Agent, or Firm* — Thomas G. Krivulka

(57) ABSTRACT

Bad odors on textile materials are often caused by body odor. The invention relates to a textile material treatment method for inhibiting body odor on textile materials, by which means the treated textiles, after having been worn, even after sweat-inducing sports activities, have a significantly reduced bad odor or even no odor. The invention also relates to a perfume composition and to a textile material treatment agent, respectively comprising urea derivatives and/or phenacylthiazolium salts, that counteract the formation of body odor.

2 Claims, No Drawings

PREVENTION OF BODY ODOUR

CROSS-REFERENCES TO RELATED APPLICATIONS

This application is a continuation of PCT/EP2010/061737, filed on Aug. 12, 2010, which claims priority under 35 U.S.C. §119 to DE 10 2009 029 370.1 filed on Sep. 11, 2009, both of which are hereby incorporated by reference.

FIELD OF THE INVENTION

The present invention generally relates to a perfume composition, a fabric treatment agent as well as a fabric treatment process for inhibiting body odors on fabrics by employing a fabric treatment agent comprising a urea derivative and/or phenacylthiazolium salts, and also relates to the use of urea derivatives and/or phenacylthiazolium salts in fabric treatment for inhibiting body odors on the fabrics.

BACKGROUND OF THE INVENTION

A large number of perfume compositions have already been developed that essentially refer to different fragrance combinations or their encapsulation or binding to certain carriers. In general, the action of the conventional perfume compositions is limited to the generation of pleasant odors.

The development of a perfume composition that when worn on the human skin hinders the formation of body odors or at least counteracts the formation of body odors, and that is also preferably suitable for use in fabric treatment agents as well as fabric treatment processes is highly desireable.

Perfume compositions of the present invention that contains urea derivatives and/or phenacylthiazolinium salts address these needs.

Furthermore, other desirable features and characteristics of the present invention will become apparent from the subsequent detailed description of the invention and the appended claims, taken in conjunction with this background of the invention.

BRIEF SUMMARY OF THE INVENTION

The present invention relates to perfume compositions containing urea derivatives and/or phenacylthiazolium salts.

The invention further includes fabric treatment agents, in particular washing agents, post-conditioners or fabric fresheners, for inhibiting body odors, in particular the odor of perspiration, on fabrics, comprising urea derivatives and/or phenacylthiazolium salts.

Furthermore, fabric treatment methods for inhibiting body odors, in particular the odor of perspiration, on fabrics, wherein the fabrics are treated in the presence of water at a temperature below 95° C. for a period of 2 minutes to 300 minutes by adding a fabric treatment agent comprising a urea derivative and/or a phenacylthiazolium salt are described.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A preferred perfume composition includes (a) one or more (monohydric and/or polyhydric) alcohols containing 2 to 8 carbon atoms in amounts of 0.1 to 80 wt %, preferably 1 to 70 wt %, especially 5 to 60 wt %.

(b) 0.001 to 50 wt %, preferably 0.01 to 30 wt %, especially 0.1 to 20 wt % of urea derivatives and/or phenacylthiazolium salts, (c) fragrances in amounts of 2 to 99.9 wt %, wt % each based on the total composition.

Inventively preferred useable alcohols are propylene glycol, ethanol, diethylene glycol, dipropylene glycol, benzyl alcohol, (2-methoxymethylethoxy)propanol, isopropanol as well as mixtures thereof.

The perfume composition according to the invention can preferably include a solubilizer for perfume oils, especially in amounts of 0.001% to 15 wt %, preferably up to 10 wt %, particularly up to 5 wt %, each based on the total composition. Solubilizers are substances that when present are capable of rendering other insoluble or at least sparingly soluble compounds in a given solvent soluble or emulsifiable in that solvent. Inventively preferred useable solubilizers are isopropyl myristate as well as fatty acid esters of ethoxylated glycerin and glycol ethers.

The perfume composition according to the invention can preferably include emulsifiers, especially in amounts of 0.001% to 10 wt %, preferably <5 wt %, particularly <2 wt %, each based on the total composition. Preferred useable emulsifiers according to the invention are ethoxylated triglycerides, such as e.g. hydrogenated castor oil containing e.g. ca. 40 or ca. 60 mol EO (commercially available from Cognis Germany as Eumulgin HRE 40 or Eumulgin HRE 60), ethoxylated fatty alcohols, such as e.g. $C_{12}$-$C_{18}$ fatty alcohols containing e.g. ca. 5 or ca. 7 mol EO (commercially available from Cognis Germany as Dehydol LT5 or Dehydol LT7.)

Preferred inventively useable urea derivatives as well as phenacylthiazolium salts will be described in detail further below.

The perfume composition according to the invention, when worn on (especially human) skin and/or hair, hinder (especially human) body odor or at least counteract its formation. The aimed effect is superior to that of conventional perfumes as these only mask the body odor. The perfume compositions according to the invention on the other hand actively prevent body odor, i.e. counteract the formation of body odor. The perfume composition, when also applied onto fabric, ensures that no body odor appears on the fabric during or after (especially human) body contact or that its formation is counteracted.

The perfume composition is preferably realized with the following fragrance contents:

- as an extract, preferably comprising fragrances in amounts of 10-25 wt %;
- as a perfume water, preferably comprising fragrances in amounts of 8-10 wt %;
- as a toilet water, preferably comprising fragrances in amounts of 5-8 wt %;
- as an Eau de Cologne, preferably comprising fragrances in amounts of 2-5 wt %, each wt % based on the total perfume composition.

However, the fragrance content of the perfume composition is preferably more than 5 wt %, advantageously more than 10 wt %, more advantageously more than 15 wt %, especially more than 20 wt %, based on the total perfume composition.

Preferred inventively useable fragrances are particularly selected from the group that includes fragrances of natural or synthetic origin, preferably readily volatile fragrances, higher boiling fragrances, solid fragrances and/or tenacious fragrances. Exemplary tenacious odoriferous substances that can be used in the context of the present invention are the ethereal oils such as angelica root oil, aniseed oil, arnica flowers oil, basil oil, bay oil, bergamot oil, champax blossom oil, silver fir oil, silver fir cone oil, elemi oil, eucalyptus oil, fennel oil, pine needle oil, galbanum oil, geranium oil, ginger grass oil, guaiacum wood oil, Indian wood oil, helichrysum oil, ho oil, ginger oil, iris oil, cajuput oil, sweet flag oil, camomile oil, camphor oil, Canoga oil, cardamom oil, cassia oil, Scotch fir oil, copaiba balsam oil, coriander oil, spearmint oil, caraway oil, cumin oil, lavender oil, lemon grass oil, lime oil, mandarin oil, melissa oil, amber seed oil, myrrh oil, clove oil, neroli oil, niaouli oil, olibanum oil, orange oil, origanum oil, Palma Rosa oil, patchouli oil, Peru balsam oil, petit grain oil, pepper oil, peppermint oil, pimento oil, pine oil, rose oil, rosemary oil, sandalwood oil, celery seed oil, lavender spike oil, Japanese anise oil, turpentine oil, thuja oil, thyme oil, verbena oil, vetiver oil, juniper berry oil, wormwood oil, wintergreen oil, ylang-ylang oil, ysop oil, cinnamon oil, cinnamon leaf oil, citronella oil, citrus oil and cypress oil. However, in the context of the present invention, the higher boiling or solid odoriferous substances of natural or synthetic origin can be used as tenacious odoriferous substances or mixtures thereof, namely fragrances. These compounds include for example the following compounds and their mixtures: ambrettolide, α-amyl cinnamaldehyde, anethol, anisaldehyde, anis alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valeriate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptyne carboxylate, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarone, p-methoxyacetophenone, methyl n-amyl ketone, methyl anthranilic acid methyl ester, p-methyl acetophenone, methyl chavicol, p-methyl quinoline, methyl-β-naphthyl ketone, methyl-n-nonyl acetaldehyde, methyl n-nonyl ketone, muscone, β-naphthol ethyl ether, β-naphthol methyl ether, nerol, nitrobenzene, n-nonyl aldehyde, nonyl alcohol, n-octyl aldehyde, p-oxyacetophenone, pentadecanolide, β-phenyl ethyl alcohol, phenyl acetaldehyde dimethyl acetal, phenyl acetic acid, pulegone, safrol, isoamyl salicylate, methyl salicylate, hexyl salicylate, cyclohexyl salicylate, santalol, scatol, terpineol, thymine, thymol, γ-undecalactone, vanillin, veratrum aldehyde, cinnamaldehyde, cinnamyl alcohol, cinnamic acid, ethyl cinnamate, benzyl cinnamate. The readily volatile fragrances particularly include the lower boiling odoriferous substances of natural or synthetic origin that can be used alone or in mixtures. Exemplary readily volatile odoriferous substances are alkyl isothiocyanates (alkyl mustard oils), butanedione, limonene, linalool, linalyl acetate and linalyl propionate, menthol, menthone, methyl n-heptenone, phellandrene, phenyl acetaldehyde, terpinyl acetate, citral, citronellal. Fragrant aldehydes, such as e.g. lyral, 1-dodecanal, 3,7-dimethyloctan-1-al, 1-undecanal, hexanal, trans-2-hexenal etc. can be preferably used. Likewise, useable fragrant ketones can preferably be selected from alpha damascone, delta damascone, iso damascone, carvone, gamma-methyl-ionone, iso-E-super, 2,4,4,7-tetramethyl-oct-6-en-3-one, benzylacetone, beta damascone, damascenone, methyl dihydrojasmonate, methyl cedrylone, hedione etc. Naturally, all fragrances that are commonly used and available to the person skilled in the art may be used in addition to the fragrances mentioned here, also independently of them.

The perfume composition according to the invention can be provided to be incorporated into other products, particularly in washing or cleaning agents, in cosmetics, in air-care products as well as in adhesives. In washing or cleaning agents, the perfume composition according to the invention can be incorporated in amounts of 0.01 to 10 wt %, preferably 1 to 5 wt %, based on the total weight of the washing or cleaning agent.

The use of washing agents for treating textile products primarily serves the consumer for cleaning the textiles, such that e.g. soil particles, colored stains as well as fatty and oily soils can be removed from the fabric. Furthermore, the consumer is interested that the fabrics not only appear to be visually clean, but also that they smell good. For this reason most washing agents comprise odoriferous substances or perfume compositions. The problem still remains that when the fabrics are being used, e.g. when underwear or sports clothes are worn, they can relatively quickly exhibit off odors, in particular resulting from perspiration or body odors, such that the otherwise actually clean washing is considered as unpleasant by the wearer.

The use of the perfume compositions according to the invention for fabric treatment now enables one to counteract the formation of off odors on the treated fabrics, resulting from perspiration and body odors, in particular such as sweat, after or when wearing the fabrics.

Another subject matter of the invention is a (preferably fragrance-containing) fabric treatment agent, in particular washing agents, post-conditioners or fabric fresheners, for inhibiting body odors, in particular the odor of perspiration, on fabrics, comprising urea derivatives and/or phenacylthiazolium salts. The fabric treatment agent according to the invention preferably comprises a perfume composition according to the invention, e.g. in amounts of 0.01 to 10 wt %, preferably 0.1 to 5 wt %, based on the total fabric treatment agent. Further possible ingredients of the fabric treatment agent according to the invention, such as e.g. active washing, care, cleaning and/or cosmetic components, will be described further below.

The combined use of the urea derivatives and/or phenacylthiazolium salts with fragrances, in particular in combination with surfactants, enables a quite particularly good, inventively intended reduction of off odors.

Another subject matter of the invention is a fabric treatment method for inhibiting body odors, in particular the odor of perspiration, on fabrics, wherein the fabrics are treated in the presence of water at a temperature below 95° C. for a period of 2 minutes to 300 minutes by adding a (preferably fragrance-containing) fabric treatment agent comprising a urea derivative and/or a phenacylthiazolium salt. The urea derivatives and/or pnenacylthiazolium salts of the fabric treatment agent are incorporated into the fabric treatment agent particularly in the form of a perfume composition according to the invention.

It was found that the fabrics treated in this way, after being worn, even after sweat-generating sports activities, exhibit a significantly lower off odor, or are even odorless. Another advantage of the method according to the invention is that sweaty odors as such are removed during the fabric treatment, as frequently even washed washing still smells of perspiration, namely particularly washing that can only be washed at low temperatures.

According to a preferred embodiment of the method according to the invention, the treatment time is in the range of 5 minutes to 240 minutes, preferably 15 minutes to 120 minutes, especially from 20 minutes to 60 minutes. According to another preferred embodiment of the method according to the invention, the temperature is in the range of 15° C. to 60° C., especially from 20° C. to 40° C.

The inventively useable urea derivative preferably concerns a sulfonyl urea, sulfonyl thiourea, acyl urea or acyl thiourea.

The sulfonyl urea concerns a compound containing the structural element

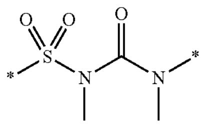 [SMILES: *N(C)C(=O)N(C)S(*)(=O)=O]

the acyl urea concerns a compound containing the structural element

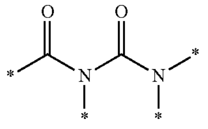 [SMILES: *C(=O)N(*)C(=O)N(*)*]

the sulfonyl thiourea concerns a compound containing the structural element

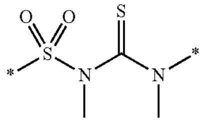 [SMILES: *N(C)C(=S)N(C)S(*)(=O)=O]

the acyl thiourea concerns a compound containing the structural element

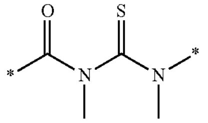 [SMILES: *C(=O)N(C)C(=S)N(*)C]

The sulfonyl urea preferably concerns a compound with the general Formula $R^1$—$SO_2$—NX—C(O)—NY—$R^2$, the acyl urea a compound with the general Formula $R^1$—C(O)—NX—C(O)—NY—$R^2$, the sulfonyl thiourea a compound with the general Formula $R^1$—$SO_2$—NX—C(S)—NY—$R^2$ and the acyl thiourea a compound with the general Formula $R^1$—C(O)—NX—C(S)—NY—$R^2$, wherein X, Y, $R^1$ and $R^2$ independently of one another stand for trifluoromethyl, hydrogen, alkyl, in particular $C_{1-22}$ alkyl, preferably $C_{1-18}$ alkyl, cycloalkyl, in particular $C_{3-8}$ cycloalkyl, cycloalkylalkyl, in particular $C_{3-8}$ cycloalkyl-$C_{1-12}$ alkyl, alkenyl, in particular $C_{2-18}$ alkenyl, alkynyl, in particular $C_{2-18}$ alkynyl, heteroalkyl, heterocycloalkyl, alkoxy, in particular $C_{1-18}$ alkoxy, alkoxyalkyl, in particular $C_{1-18}$ alkoxy-$C_{1-18}$ alkyl, alkylsulfanyl, in particular $C_{1-18}$ alkylsulfanyl, alkylsulfinyl, in particular $C_{1-18}$ alkylsulfinyl, alkylsulfonyl, in particular $C_{1-18}$ alkylsulfonyl, alkanoyl, in particular $C_{1-18}$ alkanoyl, alkanoyloxy, in particular $C_{1-18}$ alkanoyloxy, hydroxycarbonyl, alkoxycarbonyl, in particular $C_{1-18}$ alkoxycarbonyl, alkylaminocarbonyl, in particular $C_{1-18}$ alkylaminocarbonyl, alkylsulfanylcarbonyl, in particular $C_{1-18}$ alkylsulfanylcarbonyl, hydroxy, hydroxyalkyl, in particular hydroxy-$C_{1-18}$ alkyl, amino, alkylamino, in particular ($C_{1-18}$ alkyl)NH or di-($C_{1-18}$ alkyl)N, aryl, in particular $C_{6-10}$ aryl, arylalkyl, in particular $C_{6-10}$ aryl-$C_{1-12}$ alkyl, aryloxy, in particular $C_{6-10}$ aryloxy, arylamino, in particular $C_{6-10}$ arylamino, arylsulfanyl, in particular $C_{6-10}$ arylsulfanyl, arylsulfinyl, in particular $C_{6-10}$ arylsulfinyl, arylsulfonyl, in particular $C_{6-10}$ arylsulfonyl, arylcarbonyl, in particular $C_{6-10}$ arylcarbonyl, arylcarbonyloxy, in particular $C_{6-10}$ arylcarbonyloxy, aryloxycarbonyl, in particular $C_{6-10}$ aryloxycarbonyl, aryl aminocarbonyl, in particular $C_{6-10}$ arylaminocarbonyl, arylsulfanylcarbonyl, in particular $C_{6-10}$ arylsulfanylcarbonyl, heteroaryl, heteroarylalkyl, in particular heteroaryl-$C_{1-12}$ alkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylaminocarbonyl, heteroarylsulfanylcarbonyl, alkoxysulfonyl, in particular $C_{1-18}$ alkoxysulfonyl, alkoxycarbinol, in particular $C_{1-12}$ alkoxycarbinol, sulfo, sulfino, sulfeno, formyl or thioformyl, wherein all groups of the thus resulting molecules, in particular the aliphatic and aromatic groups, can each independently of each other also be optionally mono or polysubstituted, in particular mono, di or trisubstituted, preferably monosubstituted, in particular by substituents selected from the previously mentioned groups as well as selected from halogen, in particular chlorine, bromine, iodine or fluorine, and nitro.

In a particularly preferred embodiment, X stands for hydrogen and Y, $R^1$ and $R^2$ independently of each other stand for trifluoromethyl, alkyl, in particular $C_{1-22}$ alkyl, preferably $C_{1-18}$ alkyl, cycloalkyl, in particular $C_{3-8}$ cycloalkyl, cycloalkylalkyl, in particular $C_{3-8}$ cycloalkyl-$C_{1-12}$ alkyl, alkenyl, in particular $C_{2-18}$ alkenyl, alkynyl, in particular $C_{2-18}$ alkynyl, heteroalkyl, heterocycloalkyl, alkanoyl, in particular $C_{1-18}$ alkanoyl, hydroxycarbonyl, alkoxycarbonyl, in particular $C_{1-18}$ alkoxycarbonyl, alkylaminocarbonyl, in particular $C_{1-18}$ alkylaminocarbonyl, alkylsulfanylcarbonyl, in particular $C_{1-18}$ alkylsulfanylcarbonyl, aryl, in particular $C_{6-10}$ aryl, arylalkyl, in particular $C_{6-10}$ aryl-$C_{1-12}$ alkyl, arylcarbonyl, in particular $C_{6-10}$ arylcarbonyl, aryloxycarbonyl, in particular $C_{6-10}$ aryloxycarbonyl, arylaminocarbonyl, in particular $C_{6-10}$ arylaminocarbonyl, arylsulfanylcarbonyl, in particular $C_{6-10}$ arylsulfanylcarbonyl, heteroaryl, heteroarylalkyl, in particular heteroaryl-$C_{1-12}$ alkyl, heteroarylcarbonyl, heteroaryloxycarbonyl, heteroarylaminocarbonyl, heteroarylsulfanylcarbonyl or formyl, wherein Y also preferably stands for hydrogen, and wherein all groups of the thus resulting molecules, in particular the aliphatic and aromatic groups, can each independently of each other also be optionally mono or polysubstituted, in particular mono, di or trisubstituted, preferably monosubstituted, in particular by substituents selected from the previously mentioned groups as well as selected from halogen, in particular chlorine, bromine, iodine or fluorine, hydroxy, hydroxyalkyl, in particular hydroxy-$C_{1-18}$ alkyl, hydroxycarbonyl, hydroxycarbonylalkyl, in particular hydroxycarbonyl-$C_{1-18}$ alkyl, alkoxy, in particular $C_{1-18}$ alkoxy, alkoxyalkyl, in particular $C_{1-18}$ alkoxy-$C_{1-18}$ alkyl, alkoxycarbonyl, in particular $C_{1-18}$ alkoxycarbonyl, alkoxycarbonylalkyl, in particular $C_{1-18}$ alkoxycarbonyl-$C_{1-18}$ alkyl, amino, alkylamino, in particular ($C_{1-18}$ alkyl)NH or di-($C_{1-18}$ alkyl)N, alkanoyloxy, in particular $C_{1-18}$ alkanoyloxy, alkylsulfonyl, in particular $C_{1-18}$ alkylsulfonyl, arylsulfonyl, in particular $C_{6-10}$ arylsulfonyl, nitro or sulfo.

In another particularly preferred embodiment, X and Y independently of one another stand for hydrogen or $C_{1-6}$ alkyl, preferably for hydrogen, and $R^1$ and $R^2$ independently of one another for alkyl, in particular $C_{1-18}$ alkyl, aryl, in particular phenyl, or arylalkyl, in particular phenyl-$C_{1-6}$ alkyl, wherein the cited groups can each independently of each other also be optionally mono or polysubstituted, in particular by groups selected from alkyl, in particular $C_{1-18}$ alkyl, halogen, in particular chlorine, bromine or fluoro, hydroxy, hydroxyalkyl, in particular hydroxy-$C_{1-18}$ alkyl, hydroxycarbonyl, hydroxycarbonylalkyl, in particular hydroxycarbonyl-$C_{1-18}$ alkyl, alkoxy, in particular $C_{1-18}$ alkoxy, alkoxyalkyl, in particular $C_{1-18}$-Alkoxy-$C_{1-18}$ alkyl, alkoxycarbonyl, in particular $C_{1-18}$ alkoxycarbonyl, alkoxycarbonylalkyl, in particular $C_{1-18}$ alkoxy-carbonyl-$C_{1-18}$ alkyl, Amino, alkylamino, in particular ($C_{1-18}$ alkyl)NH or di-($C_{1-18}$ alkyl)N, alkanoyloxy, in particular $C_{1-18}$ alkanoyloxy, alkylsulfonyl, in particular $C_{1-18}$ alkylsulfonyl, arylsulfonyl, in particular $C_{6-10}$ arylsulfonyl, nitro or sulfo.

In another particularly preferred embodiment, X and Y stand for hydrogen, $R^1$ for an optionally substituted group selected from alkyl, in particular $C_{1-18}$ alkyl, aryl, in particular phenyl, and arylalkyl, in particular phenyl-$C_{1-6}$ alkyl, and $R^2$ for alkyl, substituted by at least one hydroxyl group, $C_{1-6}$ alkoxy group, hydroxy-$C_{1-6}$ alkyl group, $C_{1-6}$-alkoxy-$C_{1-6}$ alkyl group, hydroxycarbonyl group, hydroxycarbonyl-$C_{1-6}$ alkyl group, $C_{1-6}$-alkoxycarbonyl group or $C_{1-6}$ alkoxycarbonyl-$C_{1-6}$ alkyl group as well as optionally by additional groups, in particular $C_{1-18}$ alkyl, aryl, in particular phenyl, or arylalkyl, in particular phenyl-$C_{1-6}$ alkyl, wherein the substituents or additional groups are preferably selected from $C_{1-6}$ alkyl, in particular methyl, halogen, in particular chlorine, bromine or fluorine, as well as additional hydroxy, $C_{1-6}$ alkoxy, hydroxy-$C_{1-6}$ alkyl, $C_{1-6}$-alkoxy-$C_{1-6}$ alkyl, hydroxycarbonyl, hydroxycarbonyl-$C_{1-6}$ alkyl, $C_{1-6}$-alkoxycarbonyl or $C_{1-6}$-alkoxycarbonyl-$C_{1-6}$ alkyl groups.

In another particularly preferred embodiment, X and Y stand for hydrogen, $R^1$ for an optionally substituted phenyl and $R^2$ for alkyl, substituted by at least one hydroxyl group, $C_{1-6}$ alkoxy group, hydroxy-$C_{1-6}$ alkyl group, $C_{1-6}$-alkoxy-$C_{1-6}$ alkyl group, hydroxycarbonyl group, hydroxycarbonyl-$C_{1-6}$ alkyl group, $C_{1-6}$-alkoxycarbonyl group or $C_{1-6}$ alkoxycarbonyl-$C_{1-6}$ alkyl group as well as optionally by phenyl substituted by additional groups, wherein the substituents or additional groups are preferably selected from $C_{1-6}$ alkyl, in particular methyl, halogen, in particular chlorine, bromine or fluorine, as well as additional hydroxy, $C_{1-6}$ alkoxy, hydroxy-$C_{1-6}$ alkyl, $C_{1-6}$-alkoxy-$C_{1-6}$ alkyl, hydroxycarbonyl, hydroxycarbonyl-$C_{1-6}$ alkyl, $C_{1-6}$-alkoxycarbonyl or $C_{1-6}$-alkoxycarbonyl-$C_{1-6}$ alkyl groups.

In this quite particularly preferred embodiment, the urea derivative concerns a sulfonyl urea according to Formula (I) or (II)

(I)

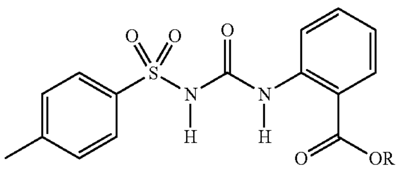

(II)

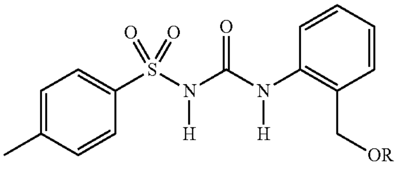

or a sulfonyl thiourea according to Formula (III) or (IV)

(III)

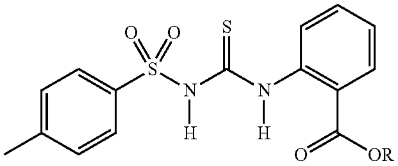

-continued (IV)

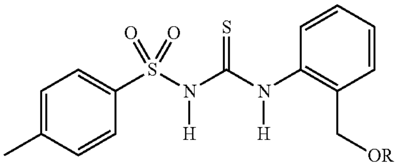

or mixtures thereof, with each R=hydrogen or $C_{1-6}$ alkyl and wherein the alkyl and aryl groups of the abovementioned compounds of the Formulas (I), (II), (III) and (IV) can each optionally carry further substituents, in particular selected from $C_{1-6}$ alkyl, in particular methyl, halogen, in particular chlorine, bromine or fluorine, as well as further hydroxyl, $C_{1-6}$ alkoxy, hydroxy-$C_{1-6}$ alkyl, $C_{1-6}$-alkoxy-$C_{1-6}$ alkyl, hydroxycarbonyl, hydroxycarbonyl-$C_{1-6}$ alkyl, $C_{1-6}$-alkoxycarbonyl or $C_{1-6}$-alkoxycarbonyl-$C_{1-6}$ alkyl groups.

The inventively useable phenacylthiazolium salt preferably includes a cation according to Formula (V)

(V)

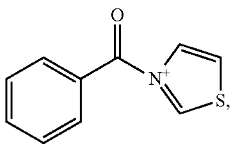

wherein this compound can also be mono or polysubstituted, preferably mono, di or trisubstituted, preferably by substituents already cited in regard to the urea derivatives, in particular by substituents selected from $C_{1-6}$ alkyl, in particular methyl, halogen, in particular chlorine, bromine or fluorine, hydroxyl, $C_{1-6}$ alkoxy, hydroxy-$C_{1-6}$ alkyl, $C_{1-6}$-alkoxy-$C_{1-6}$ alkyl, hydroxycarbonyl, hydroxycarbonyl-$C_{1-6}$ alkyl, $C_{1-6}$-alkoxycarbonyl and $C_{1-6}$-alkoxycarbonyl-$C_{1-6}$ alkyl.

The counter ion of the phenacylthiazolium cation can be any desired counter ion. In a preferred embodiment the counter ion is selected from halide anions. The compound is particularly preferably phenacylthiazolium chloride.

$C_{1-18}$ alkyl inventively stands independently of each other for any saturated linear and branched alkyl group with up to 18 carbon atoms, wherein $C_{1-6}$ alkyl groups are preferred. $C_{1-6}$ alkyl inventively stands for any saturated linear and branched alkyl group with up to 6 carbon atoms, in particular for methyl, ethyl, n-propyl, i-propyl, n-butyl, i-butyl, t-butyl as well as all isomers of pentyl and hexyl.

$C_{3-8}$ Cycloalkyl inventively stands independently of each other for all cyclic alkyl groups containing 3 carbon atoms, preferably containing 5 to 6 carbon atoms, wherein the groups can be saturated or unsaturated, in particular for cyclopentyl, cyclohexyl or cyclopentadienyl.

$C_{2-18}$ alkenyl inventively stands independently of each other for any linear and branched alkyl group with up to 18 carbon atoms, which comprise at least one double bond, wherein $C_{2-6}$ alkenyl groups are preferred. $C_{2-6}$ alkenyl inventively stands for any linear and branched alkyl group with up to 6 carbon atoms, which comprise at least one double bond, in particular for ethenyl, propenyl, i-propenyl as well as all isomers of butenyl, pentenyl and hexenyl.

$C_{2-18}$ alkynyl inventively stands independently of each other for any linear and unbranched alkyl group with up to 18 carbon atoms, which comprise at least one triple bond, wherein $C_{2-6}$ alkynyl groups are preferred. $C_{2-6}$ alkynyl inventively stands for any linear and unbranched alkyl group with up to 6 carbon atoms, which comprise at least one triple bond, in particular for ethynyl, propynyl, i-propynyl as well as all isomers of butynyl, pentynyl and hexynyl.

Heteroalkyl inventively stands independently of each other for all saturated and mono or polyunsaturated, linear or branched alkyl groups, which comprise at least one, preferably exactly one heteroatom, in particular selected from O, S and N, wherein the sum of carbon atoms and hetero atoms is preferably up to 18, particularly preferably up to 6.

Heterocycloalkyl inventively stands independently of each other for all cyclic alkyl groups, which comprise at least one, preferably exactly one heteroatom, in particular selected from O, S and N, wherein the ring is preferably three to eight membered, particularly preferably five to six membered. Examples of these are tetrahydrofuranyl, tetrahydrothiophenyl, pyrrolidinyl, 2-thiazolinyl, tetrahydrothiazolyl, tetrahydrooxazolyl, piperidinyl, piperazinyl, morpholinyl and thiomorpholinyl.

$C_{1-18}$ alkoxy inventively stands independently of each other for all saturated and unsaturated, linear and branched alkyl groups with up to 18 carbon atoms that are bonded through an oxygen atom, wherein $C_{1-6}$ alkoxy groups are preferred. $C_{1-6}$ alkoxy inventively stands independently of each other for all saturated and unsaturated, linear and branched alkyl groups with up to 6 carbon atoms that are bonded through an oxygen atom, in particular for methoxy and ethoxy.

$C_{1-18}$ alkylsulfanyl inventively stands independently of each other for all saturated and unsaturated, linear and branched alkyl groups with up to 18 carbon atoms that are bonded through a sulfur atom, wherein $C_{1-6}$ alkylsulfanyl groups are preferred. $C_{1-6}$ alkylsulfanyl inventively stands for all saturated and unsaturated, linear and branched alkyl groups with up to 6 carbon atoms that are bonded through a sulfur atom, in particular for methylsulfanyl and ethylsulfanyl.

$C_{1-18}$ alkylsulfinyl inventively stands independently of each other for all saturated and unsaturated, linear and branched alkyl groups with up to 18 carbon atoms that are bonded through an SO group, wherein $C_{1-6}$ alkylsulfonyl groups are preferred. $C_{1-6}$ alkylsulfanyl inventively stands for all saturated and unsaturated, linear and branched alkyl groups with up to 6 carbon atoms that are bonded through an SO group, in particular for methylsulfinyl and ethylsulfinyl.

$C_{1-18}$ alkylsulfonyl inventively stands independently of each other for all saturated and unsaturated, linear and branched alkyl groups with up to 18 carbon atoms that are bonded through an $SO_2$ group, wherein $C_{1-6}$ alkylsulfoxidyl groups are preferred. $C_{1-6}$ alkylsulfonyl inventively stands for all saturated and unsaturated, linear and branched alkyl groups with up to 6 carbon atoms that are bonded through an $SO_2$ group, in particular for methylsulfonyl and ethylsulfonyl.

$C_{1-18}$ alkanoyl inventively stands independently of each other for all saturated and unsaturated, linear and branched alkyl groups with up to 18 carbon atoms that are bonded through a carbonyl group, wherein $C_{1-6}$ alkanoyl groups are preferred. $C_{1-6}$ alkanoyl inventively stands for all saturated and unsaturated, linear and branched alkyl groups with up to 6 carbon atoms that are bonded through a carbonyl group, in particular for methylcarbonyl and ethylcarbonyl.

$C_{1-18}$ alkanoyloxy inventively stands independently of each other for all saturated and unsaturated, linear and branched alkyl groups with up to 18 carbon atoms that are bonded through a carbonyloxy group, wherein $C_{1-6}$ alkanoyloxy groups are preferred. $C_{1-6}$ alkanoyloxy inventively stands for all saturated and unsaturated, linear and branched alkyl groups with up to 6 carbon atoms that are bonded through a carbonoyloxy group, in particular for methanoyloxy, ethanoyloxy, n-propanoyloxy and i-propanoyloxy.

$C_{1-18}$ alkoxycarbonyl inventively stands independently of each other for all saturated and unsaturated, linear and branched alkyl groups with up to 18 carbon atoms that are bonded through an oxycarbonyl group, wherein $C_{1-6}$ alkoxycarbonyl groups are preferred. $C_{1-6}$ alkoxycarbonyl inventively stands for all saturated and unsaturated, linear and branched alkyl groups with up to 6 carbon atoms that are bonded through an oxycarbonyl group, in particular for methoxycarbonyl and ethoxycarbonyl.

$C_{1-18}$ Alkylaminocarbonyl inventively stands independently of each other for an amino carbonyl group that is mono or polysubstituted with a saturated or unsaturated, linear and branched alkyl group with up to 18 carbon atoms, wherein amino carbonyl groups that are mono or polysubstituted with $C_{1-6}$ alkyl groups, in particular monomethylamino carbonyl, dimethylamino carbonyl, monoethylamino carbonyl and diethylamino carbonyl, are preferred.

$C_{1-18}$ Alkylsulfanylcarbonyl inventively stands independently of each other for all saturated and unsaturated, linear and branched alkyl groups with up to 18 carbon atoms that are bonded through a thiocarbonyl group, wherein $C_{1-6}$ alkylsulfanylcarbonyl groups are preferred.

$C_{1-6}$ Alkylsulfanyl carbonyl inventively stands for all saturated and unsaturated, linear and branched alkyl groups with up to 6 carbon atoms that are bonded through a thiocarbonyl group, in particular for methylthiocarbonyl and ethylthiocarbonyl.

($C_{1-18}$ Alkyl)NH inventively stands independently of each other for all saturated and unsaturated, linear and branched alkyl groups with up to 18 carbon atoms that are bonded through a hydrogen amino group, wherein ($C_{1-6}$ alkyl)NH is preferred. ($C_{1-6}$ alkyl)NH inventively stands for all saturated and unsaturated, linear and branched alkyl groups with up to 6 carbon atoms that are bonded through a hydrogen amino group, in particular for $CH_3NH$ and $C_2H_5NH$.

($C_{1-18}$ Alkyl)NH inventively stands independently of each other for all saturated and unsaturated, linear and branched alkyl groups with up to 18 carbon atoms that are bonded through a ($C_{1-18}$ alkyl)amino group, wherein di-($C_{1-6}$ alkyl)N is preferred. Both the alkyl groups can here be the same or different from one another. Di-($C_{1-6}$ alkyl)N inventively stands for all saturated and unsaturated, linear and branched alkyl groups with up to 6 carbon atoms that are bonded through a ($C_{1-6}$ alkyl)amino group, in particular for $(CH_3)_2N$ and $(C_2H_5)_2N$.

$C_{6-10}$ Aryl inventively stands, in particular also in $C_{6-10}$ aryl-$C_{1-12}$ alkyl, $C_{6-10}$ aryloxy, $C_{6-10}$ arylamino, $C_{6-10}$ arylsulfanyl, $C_{6-10}$ arylsulfonyl, $C_{6-10}$ arylsulfoxidyl, $C_{6-10}$ arylcarbonyl, $C_{6-10}$ arylcarbonyloxy, $C_{6-10}$ aryloxycarbonyl, $C_{6-10}$ arylamino carbonyl and $C_{6-10}$ arylsulfanylcarbonyl, preferably for phenyl or naphthyl, particularly preferably for phenyl.

Heteroaryl inventively stands, in particular also in heteroaryl-$C_{1-12}$ alkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylamino carbonyl and heteroarylsulfanylcarbo-nyl, in so far as otherwise stated, for an at least one heteroatom selected from O-, S- and N-containing aromatic groups with 5 to 10, preferably 5 or 6, ring members, preferably selected from furanyl, thienyl, thiophenyl, pyrrolyl, isopyrrolyl, pyrazolyl, imidazolyl, oxazolyl, thiazolyl, isothiazolyl, pyridinyl, pyridazinyl, pyrimidinyl, pyrazinyl, triazinyl, benzofuranyl, benzothiophenyl, indolyl, quinolinyl, isoquinolinyl, benzimidazolyl, indazolyl, pyridofuranyl and pyridothienyl.

In $C_{6-10}$-aryl-$C_{1-12}$ alkyl and heteroarylalkyl the alkyl group can be saturated or unsaturated, branched or unbranched. Preferred groups are benzyl, phenylethyl, naphthylmethyl and naphthylethyl.

According to another preferred embodiment of the inventive method, the fabrics are man-made fiber- and/or natural fiber-based fabrics.

The natural fibers particularly include cotton, linen, wool (e.g. also including pure new wool, angora natural fiber, cashmere natural fiber, lama natural fiber, alpaca natural fiber, camel natural fiber, mohair natural fiber, vicuna natural fiber) and silk. When treating the fabric (or washability) of cotton, the temperature is not critical at all, as cotton can withstand high temperatures (e.g. 60-95° C.), but the care of wool and silk demands particular diligence because these fabrics are very sensitive towards higher temperatures.

The method according to the invention has now the advantage that when treating in particular wool- and/or silk-containing fabrics, in spite of low washing or treatment temperatures (e.g. T≤40° C., for example 10° C. to ≤30° C. or up to ≤20° C.), of obtaining a particularly efficient removal of odors that arise from perspiration, in particular sweat. According to another preferred embodiment of the inventive method, the fabrics are therefore fabrics containing a wool and/or silk fraction. Of course, the fabrics can also be purely of silk or wool, e.g. a silk blouse or woollen socks. However, fiber mixtures that contain silk and/or wool in addition to other fibers, such as e.g. cotton, are also preferred.

Generally, man-made fibers are also temperature-sensitive and are mostly washed at temperatures ≤60° C., e.g. at temperatures ≤40° C. (for example 10° C. to ≤30° C. or up to ≤20° C.). The same advantage results, namely that in spite of low washing or treatment temperatures, one obtains a particularly efficient removal of odors that arise from perspiration, in particular sweat. According to another preferred embodiment of the inventive method, the fabrics are therefore fabrics with a man-made fiber content, e.g. viscose or polyester. Of course, the fabrics can also be made entirely of man-made fibers, e.g. a viscose shirt. However, fiber mixtures that contain man-made fibers, such as e.g. viscose or polyester together with other fibers, such as e.g. cotton, are also preferred.

It is particularly advantageous when the method according to the invention is carried out in an automatic washing machine. According to another preferred embodiment of the method according to the invention, the urea derivative and/or phenacylthiazolium salt contacts the fabric to be treated in the course of the wash cycle and/or the rinse cycle.

In the method according to the invention, the concentration of the inventively added urea derivative and/or phenacylthiazolium salt in the aqueous treatment liquor is in the range of 0.001 g/l to 0.6 g/l, especially 0.01 g/l to 0.3 g/l.

Another subject matter of the invention is in the use of urea derivatives and/or phenacylthiazolium salts in the fabric treatment for inhibiting body odors on the fabrics.

In this regard it is particularly preferred that the urea derivatives and/or phenacylthiazolium salts are present as an ingredient of a (odoriferous substance-containing) fabric treatment agent, in particular of a washing agent, of a post-conditioning agent (such as for example fabric softener, hygienic rinse) or of a fabric freshener. This corresponds to a preferred embodiment of the method according to the invention. The agents according to the invention preferably comprise the inventively useable urea derivatives and/or phenacylthiazolium salts in an amount of up to 20 wt %, particularly preferably in amounts of 0.001 to 10 wt %, especially from 0.01 to 5 wt %, above all from 0.1 to 2 wt %.

If the inventive use occurs in the context of a washing process for laundry, in particular in an automatic washing machine, then this is once again a preferred embodiment of the invention.

Fabric treatment agents according to the invention have already been cited above, these also include e.g. the fabric fresheners. Particularly preferred fabric fresheners are liquid agents for spraying fabrics at home; the agents preferably comprise still further ingredients in addition to the urea derivatives and/or phenacylthiazolium salts in order to absorb volatile, unpleasant smelling molecules and especially to cover up or mask them with pleasant fragrances. Cyclodextrins and/or ricinoleates (such as zinc ricinoleate in particular) can be added in particular for the absorption.

According to another preferred embodiment, the fabric treatment agent according to the invention possesses at least one, preferably a plurality of active components, in particular active washing, care, cleaning components and/or cosmetic components, advantageously selected from the group containing anionic surfactants, cationic surfactants, amphoteric surfactants, non-ionic surfactants, acidifiers, alkalizers, anti-crease agents, antibacterials, antioxidants, anti-redeposition agents, antistats, builders, bleaching agents, bleach activators, bleach stabilizers, bleach catalysts, ironing auxiliaries, co-builders, fragrances, shrink preventers, electrolytes, enzymes, color protection agents, colorants, dyes, color transfer inhibitors, fluorescence agents, fungicides, germicides, odor-complexing substances, auxiliaries, hydrotropes, rinse agents, complexants, preservatives, corrosion inhibitors, water-miscible organic solvents, optical brighteners, perfumes, perfume carriers, pearlizers, pH-adjustors, water repellants and impregnation agents, polymers, swelling and non-skid agents, foam inhibitors, layered silicates, soil-repellant substances, silver-protection agents, silicone oils, soil release active substances, UV-protection agents, viscosity regulators, thickeners, discoloration inhibitors, anti-graying inhibitors, vitamins and/or fabric softeners. In the context of this invention, data for the inventive fabric treatment agent are given, unless otherwise stated, in wt %, based on the total weight of the inventive fabric treatment agent.

The quantities of the individual ingredients in the inventive fabric treatment agents are each dependent on the purpose of the agent in question and as far as orders of magnitude are concerned they are entrusted to the person skilled in the art or they can be found in the appropriate technical literature. For example, the surfactant content selected for the compositions according to the invention will be relatively high or relatively low according to the intended application. The surfactant content of laundry detergents is normally between e.g. 10 and 50 wt %, preferably between 12.5 and 30 wt % and more particularly between 15 and 25 wt %, whereas fabric softeners, for example, can contain between 5 and 30 wt %, preferably between 10 and 20 wt % of surfactants.

According to another preferred embodiment of the invention, the inventive fabric treatment agent comprises fragrance(s). Exemplary, particularly suitable fragrances have already been cited above. The content of fragrances in the inventive fabric treatment agent is preferably 0.001 wt % to 10 wt %, advantageously 0.01 to 5 wt % and especially 0.1 wt % to 3 wt %, the wt % being based on the total fabric treatment agent.

The inventive fabric treatment agents can comprise surfactants, wherein particularly anionic surfactants, non-ionic surfactants and their mixtures, but also cationic surfactants come into consideration. Suitable non-ionic surfactants are particularly ethoxylation and/or propoxylation products of alkyl glycosides and/or of linear or of branched alcohols, each with 12 to 18 carbon atoms in the alkyl moiety and 3 to 20, preferably 4 to 10 alkyl ether groups. Moreover, corresponding ethoxylation and/or propoxylation products of N-alkylamines, vicinal diols, fatty acid esters and fatty acid amides, which in regard to the alkyl moiety correspond to the cited long chain alcohol derivatives, as well as of alkyl phenols with 5 to 12 carbon atoms in the alkyl group, can be used.

Suitable anionic surfactants are particularly soaps and such that comprise sulfate or sulfonate groups, preferably with alkali metal ions as the cations. Useable soaps are preferably the alkali metal salts of the saturated or unsaturated fatty acids containing 12 to 18 carbon atoms. These types of fatty acids can also be used in a not completely neutralized form. The useable surfactants of the sulfate type include the salts of sulfuric acid half esters of fatty alcohols with 12 to 18 carbon atoms and the sulfation products of the mentioned non-ionic surfactants with a low degree of ethoxylation. The useable surfactants of the sulfonate type include linear alkylbenzene sulfonates with 9 to 14 carbon atoms in the alkyl moiety, alkyl sulfonates with 12 to 18 carbon atoms, as well as olefin sulfonates with 12 to 18 carbon atoms, which result from the reaction of corresponding monoolefins with sulfur trioxide, as well as alpha-sulfofatty acid esters that result from the sulfonation of fatty acid methyl or ethyl esters.

Cationic surfactants are preferably selected from the esterquats and/or the quaternary ammonium compounds (QUATS) according to the general formula (R')(R'')(R''')($R^{IV}$)$N^+$ $X^-$, in which R' to $R^{IV}$ may be the same or different $C_{1-22}$ alkyl groups, $C_{7-28}$ arylalkyl groups or heterocyclic groups, wherein two or—in the case of an aromatic structure, such as in pyridine—even three groups, together with the nitrogen atom, form the heterocycle, for example a pyridinium or imidazolinium compound, and $X^-$ represents halide ions, sulfate ions, hydroxide ions or similar anions.

Among esterquats should here be understood compounds of the general Formula VI, (VI)

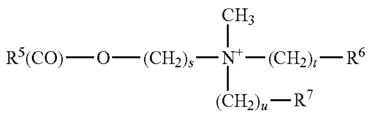

in which $R^5$ stands for an alkyl or alkenyl group containing 12 to 22 carbon atoms and 0, 1, 2 or 3 double bonds, $R^6$ and $R^7$ independently of one another stand for H, OH or O(CO)$R^5$, s, t and u each independently of one another stands for the value 1, 2 or 3 and $X^-$ stands for an anion, in particular halide, methosulfate, methophosphate or phosphate as well as mixtures thereof. Examples of compounds of Formula (VI) are methyl-N-(2-hydroxyethyl)-N,N-di(tallowacyloxyethyl)ammonium methosulfate, bis(palmitoyl)ethylhydroxyethylmethylammonium methosulfate or methyl-N,N-bis(acyloxyethyl)-N-(2-hydroxyethyl)ammonium methosulfate.

The inventive fabric treatment agents can comprise surfactants in quantities of preferably 5 wt % to 50 wt %, especially from 8 wt % to 30 wt %. Preferably up to 30 wt %, especially 5 wt % to 15 wt % of surfactants, among which at least partially are preferably cationic surfactants, are employed in particular in laundry conditioners.

An inventive fabric treatment agent preferably comprises at least one water-soluble and/or water-insoluble organic and/or inorganic builder. The water-soluble organic builders include polycarboxylic acids, particularly citric acid and sugar acids, monomeric and polymeric amino polycarboxylic acids, particularly methyl glycine diacetic acid, nitrilotriacetic acid and ethylenediamine tetraacetic acid as well as polyaspartic acid, polyphosphonic acids, particularly amino tris (methylene phosphonic acid), ethylenediaminetetrakis (methylene phosphonic acid) and 1-hydroxyethane-1,1-diphosphonic acid, polymeric hydroxyl compounds such as dextrin as well as polymeric (poly)carboxylic acids, polymeric acrylic acids, methacrylic acids, maleic acids and mixed polymers thereof, which can also comprise small amounts of copolymerized polymerizable substances exempt from carboxylic acid functionality.

Organic builders can be comprised as desired in amounts of up to 40 wt %, particularly up to 25 wt % and preferably from 1 wt % to 8 wt %. Amounts close to the cited upper limit are preferably added in pasty or liquid, particularly aqueous, inventive fabric treatment agents. Inventive laundry conditioners, such as e.g. fabric softeners, can optionally also be exempt of organic builders.

Alkali metal silicates and polyphosphates, preferably sodium triphosphate are especially used as the water-soluble inorganic builders. In particular, crystalline or amorphous alkali metal aluminosilicates in amounts of up to 50 wt %, preferably not more than 40 wt % and in liquid agents not more than 1 wt % to 5 wt % are added as the water-insoluble, water-dispersible inorganic builders. Among these, the detergent-quality crystalline sodium aluminosilicates, particularly zeolites A, P and optionally X, are preferred. Amounts close to the cited upper limit are preferably incorporated in solid, particulate agents. Suitable aluminosilicates particularly exhibit no particles with a particle size above 30 μm and preferably consist to at least 80 wt % of particles smaller than 10 μm.

Suitable substitutes or partial substitutes for the cited aluminosilicate are crystalline alkali metal silicates that can be alone or present in a mixture with amorphous silicates. The alkali metal silicates that can be used as builders in the inventive agents preferably have a molar ratio of alkali metal oxide to $SiO_2$ below 0.95, particularly 1:1.1 to 1:12 and can be amorphous or crystalline. Preferred alkali metal silicates are the sodium silicates, particularly the amorphous sodium silicates, with a molar ratio $Na_2O$: $SiO_2$ of 1:2 to 12.8.

Builders are preferably comprised in the inventive fabric treatment agents in amounts of up to 60 wt %, particularly from 5 wt % to 40 wt %. Inventive laundry conditioners, such as e.g. fabric softeners, are preferably exempt from inorganic builders.

Suitable peroxygen compounds particularly include organic peracids or peracid salts of organic acids, such as phthalimide percaproic acid, perbenzoic acid or salts of diperoxydodecanedioic acid, hydrogen peroxide and inorganic salts that liberate hydrogen peroxide under the application conditions, such as perborate, percarbonate and/or persilicate. If it is intended to use solid peroxygen compounds, then they can be used in the form of powders or pellets, which in principle can also be encapsulated by known methods. Alkali percarbonate, alkali perborate monohydrate or particularly in liquid fabric treatment agents, hydrogen peroxide in the form of aqueous solutions that comprise 3 wt % to 10 wt % hydrogen peroxide are optionally particularly preferably used. When an inventive fabric treatment agent comprises bleaching agents, such as preferably peroxygen compounds then the latter are present in amounts of preferably up to 50 wt %, especially from 5 wt % to 30 wt %. The addition of minor quantities of known bleaching agent stabilizers, such as for example phosphonates, borates or metaborates and metasilicates as well as magnesium salts such as magnesium, can be useful.

Bleach activators, which can be used, are compounds which, under perhydrolysis conditions, yield aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Polyacylated alkylenediamines, especially tetraacetylethylenediamine (TAED) are preferred. Combinations of conventional bleach activators may also be used. These types of bleach activators can be comprised in the usual quantity range of preferably 1 to 10 wt %, particularly 2 wt % to 8 wt %, based on the total fabric treatment agent.

Employable enzymes in the fabric treatment agents can include those from the classes of the proteases, cutinases, amylases, pullulanases, hemicellulases, cellulases, lipases, oxidases and peroxidases as well as mixtures thereof. They can be comprised in the inventive fabric treatment agents preferably in amounts of not more than 5 wt %, particularly from 0.2 wt % to 2 wt %.

Organic solvents that can be employed in the inventive fabric treatment agents, particularly when the agents are in liquid or paste form, include alcohols with 1 to 4 carbon atoms, particularly methanol, ethanol, isopropanol and tert-butanol, diols with 2 to 4 carbon atoms, particularly ethylene glycol and propylene glycol, their mixtures and the ethers derived from the cited classes of compounds. These types of water-miscible solvents are preferably present in the inventive agents in amounts of not more than 30 wt %, particularly 6 wt % to 20 wt %.

According to a preferred embodiment, the inventive teaching can be used in order to significantly decrease the perfume content in washing, cleaning and body care agents. This enables perfumed products to be offered even to those particularly sensitive consumers, who, due to specific intolerances and irritations, can only make limited use or are absolutely unable to use normally perfumed products.

A preferred inventive solid, especially powdered washing agent can especially comprise, in addition to the inventive ingredients (i.e. urea derivatives and/or phenacylthiazolium salts), further components that are e.g. selected from the following:

anionic surfactants, such as preferably alkylbenzene sulfonate, alkyl sulfate, e.g. in amounts of preferably 5-30 wt %
non-ionic surfactants, such as preferably fatty alcohol polyglycol ethers, alkyl polyglucoside, fatty acid glucamide e.g. in amounts of preferably 0.5-15 wt %
builders, such as e.g. zeolite, polycarboxylate, sodium citrate, in amounts of e.g. 0-70 wt %, advantageously 5-60 wt %, preferably 10-55 wt %, especially 15-40 wt-%,
alkalis, such as e.g. sodium carbonate, in amounts of e.g. 0-35 wt %, advantageously 1-30 wt %, preferably 2-25 wt %, especially 5-20 wt %,
bleaching agents, such as e.g. sodium perborate, sodium percarbonate, in amounts of e.g. 0-30 wt %, advantageously 5-25 wt %, preferably 10-20 wt-%,
corrosion inhibitors, e.g. sodium silicate, in amounts of e.g. 0-10 wt %, advantageously 1-6 wt %, preferably 2-5 wt %, especially 3-4 wt %,
stabilizers, e.g. phosphonates, advantageously 0-1 wt %,
foam inhibitors, e.g. soaps, silicone oils, paraffins advantageously 0-4 wt %, preferably 0.1-3 wt %, especially 0.2-1 wt %,
enzymes, e.g. proteases, amylases, cellulases, lipases, advantageously 0-2 wt %, preferably 0.2-1 wt %, especially 0.3-0.8 wt %,
graying inhibitors, e.g. carboxymethyl cellulose, advantageously 0-1 wt %,
discoloration inhibitors, e.g. polyvinyl pyrrolidone derivatives, preferably 0-2 wt %,
adjustment means, e.g. sodium sulfate, advantageously 0-20 wt %,
optical brighteners, e.g. stilbene derivatives, biphenyl derivatives, advantageously 0-0.4 wt %, especially 0.1-0.3 wt %,
optionally fragrances
optionally water
optionally soap
optionally bleach activators
optionally cellulose derivatives
optionally soil repellants, each wt % based on the total agent.

In another preferred embodiment of the invention, the washing, cleaning or care agent is in liquid form, preferably in gel form. Preferred liquid washing, cleaning or care agents have water contents of e.g. 10-95 wt %, preferably 20-80 wt % and especially 30-70 wt %, based on the total agent. In the case of liquid concentrates, the water content can also be particularly low, e.g. <30 wt %, preferably <20 wt %, especially <15 wt %, each wt % based on the total agent. The liquid agents can also comprise non-aqueous solvents.

A preferred inventive liquid washing agent, especially in gel form, can especially comprise, in addition to the inventive ingredients (i.e. urea derivatives and/or phenacylthiazolium salts), further components that are e.g. selected from the following:

anionic surfactants, such as preferably alkylbenzene sulfonate, alkyl sulfate, e.g. in amounts of preferably 5-40 wt %
non-ionic surfactants, such as preferably fatty alcohol polyglycol ethers, alkyl polyglucoside, fatty acid glucamide e.g. in amounts of preferably 0.5-25 wt %
builders, such as e.g. zeolite, polycarboxylate, sodium citrate, advantageously 0-15 wt %, preferably 0.01-10 wt %, especially 0.1-5 wt %,
foam inhibitors, e.g. soaps, silicone oils, paraffins, in amounts of e.g. 0-10 wt %, advantageously 0.1-4 wt %, preferably 0.2-2 wt %, especially 1-3 wt %,
enzymes, e.g. proteases, amylases, cellulases, lipases, in amounts of e.g. 0-3 wt %, advantageously 0.1-2 wt %, preferably 0.2-1 wt %, especially 0.3-0.8 wt %,
optical brighteners, e.g. stilbene derivatives, biphenyl derivatives, in amounts of e.g. 0-1 wt %, advantageously 0.1-0.3 wt %, especially 0.1-0.4 wt %,
optionally fragrances
optionally stabilizers,
water
optionally soaps, in amounts of e.g. 0-25 wt %, advantageously 1-20 wt %, preferably 2-15 wt %, especially 5-10 wt %,
optionally solvents (preferably alcohol), advantageously 0-25 wt %, preferably 1-20 wt %, especially 2-15 wt %, each wt % based on the total agent.

A preferred inventive liquid fabric softener can especially comprise, in addition to the inventive ingredients (i.e. urea derivatives and/or phenacylthiazolium salts), further components that are e.g. selected from the following:

- cationic surfactants, such as especially ester quats, e.g. in amounts of 5-30 wt %,
- co-surfactants, such as e.g. glycerine monostearate, stearic acid, fatty alcohols, fatty alcohol ethoxylates, e.g. in amounts of 0-5 wt %, preferably 0.1-4 wt %,
- emulsifiers, such as e.g. fatty amine ethoxylates, e.g. in amounts of 0-4 wt %, preferably 0.1-3 wt %,
- optionally fragrances
- colorants, preferably in the ppm range
- stabilizers, preferably in the ppm range
- solvents, such as especially water, in amounts of preferably 60-90 wt %, each wt % based on the total agent.

EXAMPLES

Example 1

Synthesis Example 1.1 Production of a Sulfonyl Urea 1.1.1. Reaction of Tosyl Sulfonic Acid Isocyanate with Methyl Anthranilate

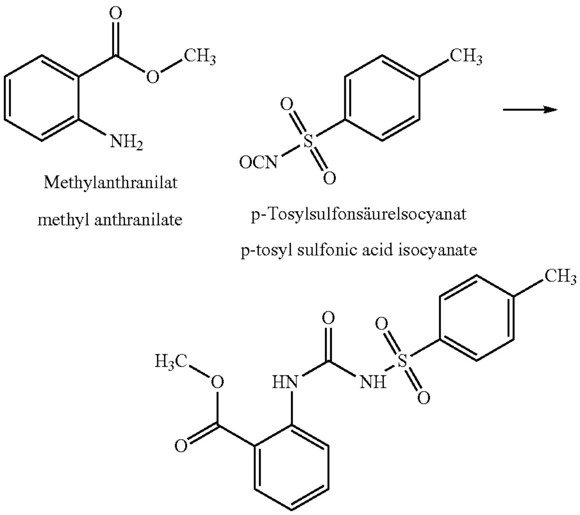

Methylanthranilat
methyl anthranilate p-Tosylsulfonsäurelsocyanat
p-tosyl sulfonic acid isocyanate In a 250 ml three-necked flask, 4.38 g (28.7 mmol) of methyl anthranilate were dissolved in 20 ml dichloromethane under a nitrogen atmosphere. 5.96 g (28 7 mmol) of p-tosyl sulfonic acid isocyanate were dissolved in 20 ml dichloromethane and slowly added drop wise at 0° C. over a period of one hour. The mixture was stirred overnight. The solvent was then removed under vacuum. A clear, colorless highly viscous oil was obtained. The remaining solvent was removed by means of a heating bath until the onset of crystallization. Further crystallization took place in a fridge and then drying under vacuum. Yield: 9.7 g (27.8 mmol, 97%).

TC (toluene/ethyl acetate 3:1): $R_f$=0.17-0.23

$^1$H-NMR (400 MHz, $CDCl_3$, TMS): δ=8.30 (d, 1H, H-2), 8.03 (d, 1H, H-5), 7.95 (d, 2H, H-8), 7.50 (t, 1H, H-4), 7.30 (d, 2H, H-9), 7.10 (t, 1H, H-3), 4.00 (s, 3H, H-1), 2.42 (s, 3H, H-10).

1.1.2. Saponification

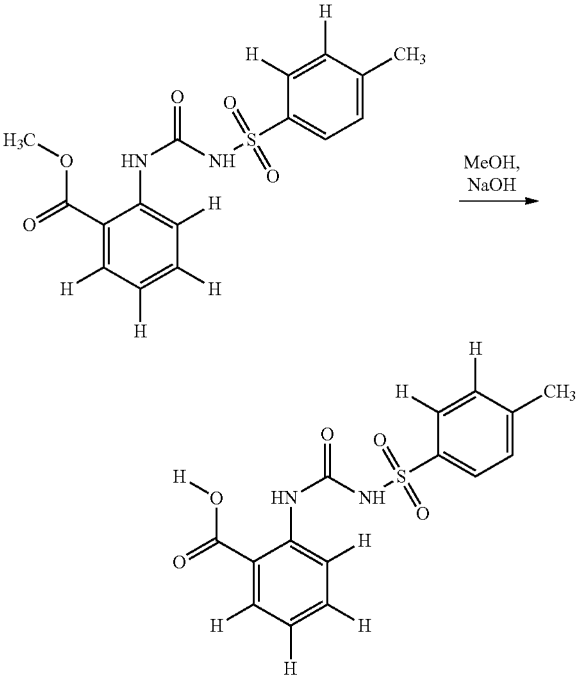

In a 100 ml three-necked flask, 2.5 g (7.2 mmol) of the starting material was dissolved in 62 ml methanol. The pH was then adjusted to pH 9 with 2M caustic soda and heated under reflux for 2 hours. After a control by TC (toluene/ethyl acetate 3:1) the heating under reflux was continued for a further 4 hours. As the reaction was still not terminated, a few chips of solid sodium hydroxide were added and the heating under reflux was continued for 6 hours. The mixture was neutralized with (glacial) acetic acid and the pH was adjusted to pH 5. The solvent was removed under vacuum to afford a yellow oil. Attempts to dissolve in toluene, ethyl acetate and dichloromethane for purification through a filter column were unsuccessful. A cloudy mixture was obtained after adding water. After adding ethyl acetate a colorless solid crystallized out which was filtered off with suction. Yield: 1.1 g (3.3 mmol, 46%).

TC (toluene/ethyl acetate 3:1): $R_f$=0

$^1$H-NMR (400 MHz, DMSO, DMSO): δ=10.35 (br. S, 1H, COOH), 8.39 (d, 1H, Ar—H), 7.86 (d, 1H, Ar—H), 7.70 (d, 2H, Ar—H), 7.36 (t, 1H, Ar—H), 7.22 (d, 2H, Ar—H), 6.83 (t, 1H, Ar—H), 2.33 (s, 3H, Ar—$CH_3$).

2.2. Synthesis of Phenacylthiazolium Chloride

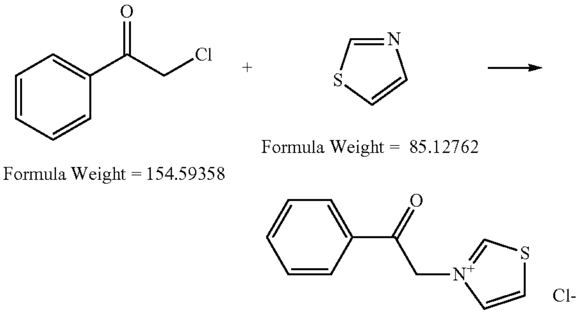

Formula Weight = 154.59358

Formula Weight = 85.12762

Formula Weight = 239.7206514

15.46 g (0.10 mol) of 2-chloroacetophenone was weighed out and dissolved in 60 ml ethyl acetate. The clear solution was heated to 75° C. and 4.4 ml (0.0624 mmol) thiazole was added drop wise with stirring. The resulting clear solution was then stirred under reflux for 3.5 hours and then allowed to stand under a nitrogen atmosphere for one day; the resulting suspension was filtered off under suction and dried in a high vacuum. Yield: 1.94 g (13%).

Example II

Washing Tests i) added washing agent:

washing agent (a) commercial powdered washing agent; dose: 80 g washing agent (b) commercial powdered washing agent, but containing 1 wt % sulfonyl urea (added with perfume oil); dose: 80 g washing agent (c) commercial powdered washing agent, but containing 1 wt % phenacylthiazolium chloride (added with perfume oil); dose: 80 g ii) washing conditions Miele washing machine W 1734 WPS main wash cycle: 40° C.

quantity of fabrics: 3.0 kg

Spin: 1200 rpm iii) washing:

a) men's shirts (100% cotton)

b) sport fabrics (100% polyester)

The men's shirts (100% cotton) were each separately washed with the washing agents (a), (b) and (c) and dried on a washing line. They were then subjected by 5 perfumers to an olfactory examination for sweaty odors and evaluated on a scale of 0 to 10 (0=no smell of sweat to 10=very strong smell of sweat). The shirts were then subjected to a wearing test, i.e. worn by test persons, who wore the shirts directly on the skin for a period of 8 hours. The test persons had not used any deodorant. After the 8-hour wearing test the men's shirts were again subjected by the same group of perfumers to an olfactory examination for sweaty odors, wherein they were again evaluated on a scale of 0 to 10. The results are summarized further below. The recorded values are the average values from the evaluations of the perfumers.

The sport fabrics (100% polyester) were likewise each separately washed with the washing agents (a), (b) and (c) and dried on a washing line. They were then subjected by 5 perfumers to an olfactory examination for sweaty odors and evaluated on a scale of 0 to 10 (0=no smell of sweat to 10=very strong smell of sweat). The sport fabrics were then subjected to a wearing test, i.e. worn by test persons, who then went jogging for a period of 2 hours. The sport fabrics were worn directly on the skin. The test persons had not used any deodorant. After the 8-hour wearing test the sport fabrics were again subjected by the same group of 5 perfumers to an olfactory examination for sweaty odors, wherein they were again evaluated on a scale of 0 to 10. The results are likewise summarized further below. The recorded values are the average values from the evaluations of the perfumers.

| | Intensity of the sweaty odor before the wearing test men's shirts 100% cotton | Intensity of the sweaty odor after the (8 h) wearing test men's shirts 100% cotton |
|---|---|---|
| Washing agent (a) | 0 | 6.1 |
| Washing agent (b) | 0 | 2.8 |
| Washing agent (c) | 0 | 3.9 |

| | Intensity of the sweaty odor before the wearing test sport fabric 100% polyester | Intensity of the sweaty odor after the (2 h sport) wearing test sport fabric 100% polyester |
|---|---|---|
| Washing agent (a) | 0 | 8.2 |
| Washing agent (b) | 0 | 2.9 |
| Washing agent (c) | 0 | 4.8 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A perfume composition comprising sulfonyl thioureas according to Formula (IV)

(IV)

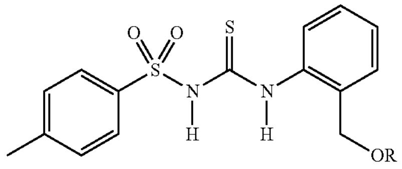

with R=hydrogen or $C_{1-6}$ alkyl.

2. A fabric treatment agent for inhibiting body odors on fabrics comprising the perfume composition according to claim 1 and at least one component selected from the group consisting of anionic surfactants, cationic surfactants, amphoteric surfactants, non-ionic surfactants, acidifiers, alkalizers, antibacterials, antioxidants, ant-redeposition agents, builders, bleaching agents, bleach activators, bleach stabilizers, bleach catalysts, co builders, fragrances, electrolytes, enzymes, color protection agents, colorants, dyes, color transfer inhibitors, fluorescence agents, fungicides, germicides, odor-complexing substances, rinse agents, preservatives, corrosion inhibitors, water-miscible organic solvents, optical brighteners, perfumes, pearlizers, pH-adjustors, water repellants and impregnation agents, polymers, foam inhibitors, layered silicates, soil-repellant substances, silicone oils, soil release active substances, UV-protection agents, viscosity regulators, thickeners, discoloration inhibitors, anti-graying inhibitors, vitamins and/or fabric softners.

* * * * *